(12) United States Patent
Wojnarowski et al.

(10) Patent No.: US 6,262,573 B1
(45) Date of Patent: Jul. 17, 2001

(54) ELECTROMAGNETIC SYSTEM FOR RAILROAD TRACK CRACK DETECTION AND TRACTION ENHANCEMENT

(75) Inventors: Robert John Wojnarowski, Ballston Lake; Kenneth Brakeley Welles, II, Scotia; William Paul Kornrumpf, Schenectady, all of NY (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/397,839

(22) Filed: Sep. 17, 1999

(51) Int. Cl.[7] .............. B61K 9/10; G01N 27/82
(52) U.S. Cl. .............................................. 324/217
(58) Field of Search ........................ 324/217, 218, 324/228, 219, 226, 232, 233, 234, 236, 237, 239, 240, 242, 243, 260, 262; 246/122 R, 121, 168.1

(56) References Cited

U.S. PATENT DOCUMENTS

| | | | |
|---|---|---|---|
| 4,179,744 | * 12/1979 | Lowe | 364/551 |
| 4,979,392 | * 12/1990 | Gunion | 73/146 |
| 5,579,013 | * 11/1996 | Hershey et al. | 324/357 |

* cited by examiner

*Primary Examiner*—Jay Patidar
*Assistant Examiner*—Renna Aurora
(74) *Attorney, Agent, or Firm*—Jill M. Breedlove; Douglas E. Stoner

(57) ABSTRACT

An electromagnetic system for detecting cracked rail and enhancing traction when necessary, includes wiring coils around wheel axles, and a corresponding power source for supplying power to the coils for producing electromagnetic flux. The produced electromagnetic flux is routed through the wheel axles, wheels and rails in a closed circuit. When a cracked rail is encountered along the route, the circuit will be interrupted or open, resulting in a changed flux pattern. This pattern change is detected by a flux sensor, and the geographic location of the crack in the rail is determined. The electromagnetic system further includes an electromagnetic wheel loading means for generating an attraction to the rails. The generated attraction to the rails increases friction between the wheels and the rails, thereby increasing traction to enable hauling greater loads up steep grades.

20 Claims, 6 Drawing Sheets

ELECTROMAGNETIC SYSTEM FOR RAILROAD TRACK CRACK DETECTION AND TRACTION ENHANCEMENT

TECHNICAL FIELD

This invention relates to train rail crack detection and traction enhancement and, more particularly, to detection of a cracked train rail by magnetic flux and, additionally, to the increase of traction between a train wheel and the rail, again by magnetic flux.

BACKGROUND ART

Cracked rails occur in various geographical areas, in various climates, and at various locations where the rail beds are in less than optimal condition. Undetected cracked rails can cause derailment along with life-threatening danger and equipment damage. Currently, ten mile areas of rail track are probed before a train is allowed to go on the track. The probing creates a delay and backup in freight car areas and in locomotive dispatching, where cost to shipping is added due to these idle waiting rail cars.

It is desirable to know the condition of a section of track as the train leaves that section of the track. Self-policing track by simple low cost means for the next user, which may be closer than the ten mile probe area, would allow closer spacing of trains and thus increase throughput of coal etc., throughout the rail system.

All sorts of schemes have been conceived to detect cracks in a rail, but none appear to be cost effective. Ultrasound, and the like, employ detectors to screen out known discontinuities in track mating techniques, but none are cost effective to date.

Further problems occur when train locomotives pull heavy loads under various types of weather, track condition, etc. Wheel slippage causes damage to tracks and wheels themselves. Various techniques have been tried to detect loss of traction as well as slippage and re-direct power to the non-slipping wheels. This resembles the limited slip or traction control offered in many automobiles. Such techniques have had varying degrees of success.

It is desired to greatly increase traction to enable locomotives to pull greater loads up hills. Maintenance of damaged wheels and track due to slippage is time-consuming and costly. Therefore, the desire to minimize or eliminate slippage is another issue for the subject of the present invention.

SUMMARY OF THE INVENTION

A method to detect train rail cracks easily, and at low cost, is implemented with a circuit for detection of cracks in train rails and rail discontinuity. The invention provides both train truck and trailering embodiments for rail crack detection with little complexity.

The invention also involves use of a method of magnetraction to inhibit slippage between train wheel and track, using electromagnetic energy with no current in or through the train axle bearing. The method uses opposing electromagnetic fields to generate and complete the magnetic circuit, enabling both aspects of this invention to take place. An electromagnet structure is used to pull the train locomotive downward toward the track, thus increasing the loading force on the wheel, producing greater friction and therefore improved traction. A train operator can apply this magnetraction at will, or under computer control.

A preferred embodiment of the invention combines a crack detector and traction enhancement concept for locomotive and end of train crack detection. The magnetic structure force enhancer is placed where it will not interfere with proper operation of the train. Additionally, the invention provides a way to use electromagnetic energy that does not require electric current in the bearing assemblies of the train axles.

An electromagnetic system for rail detection and traction enhancement comprises, in a preferred embodiment, wheel axles, wiring coils around the wheel axles, respectively, and a power source coupled to the wiring coils for supplying power to produce electromagnetic flux. The wiring coils produce opposite magnetic north and south pole pairs on the axles.

The electromagnetic system further comprises means for monitoring a flux pattern if different, interrupted or open, and means for locating the position where the circuit pattern is detected as open. The power source is a generator for generating power by wheel rotation, or by a locomotive engine. The system further includes an electromagnetic wheel loading means connected to said power source, for generating artificial load of a train.

PREFERRED EMBODIMENT OF THE INVENTION

Figure 1:
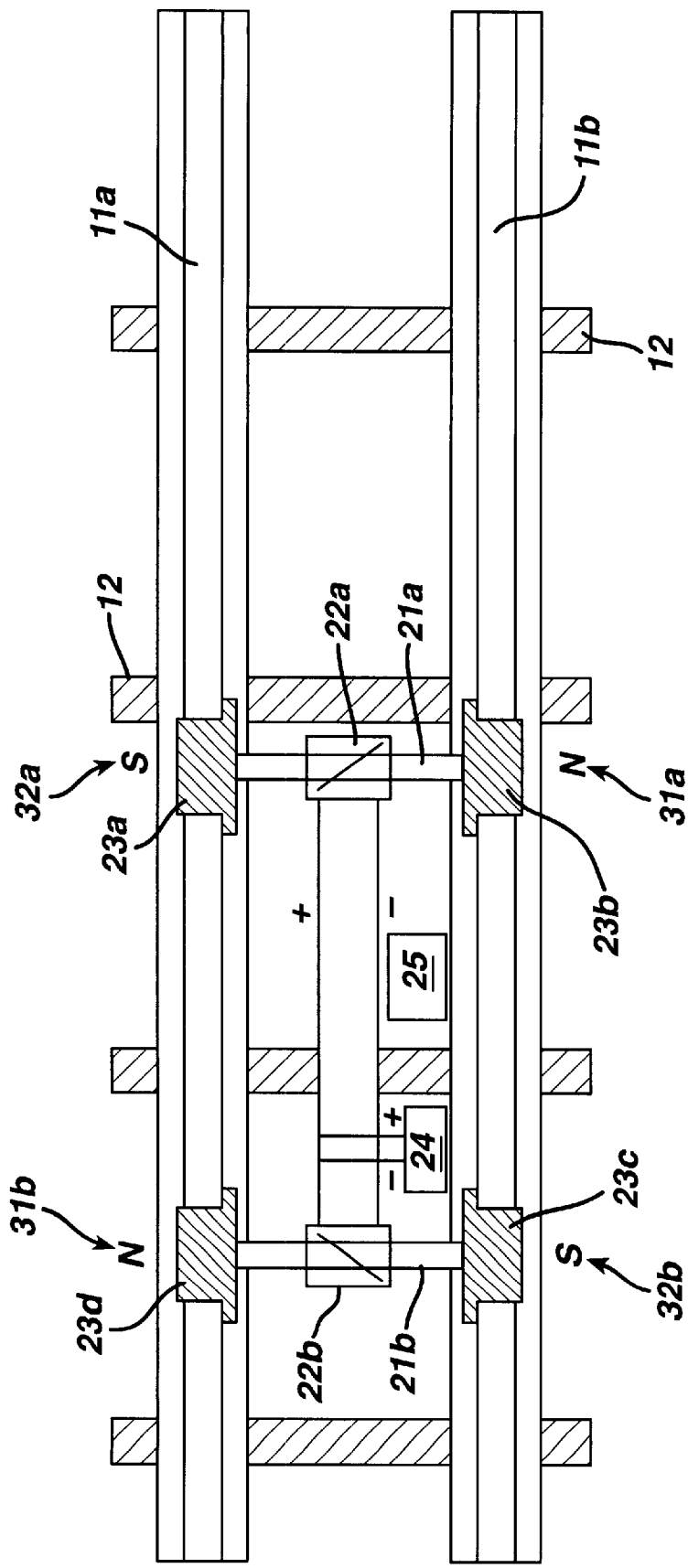
FIG. 1 is a schematic view of the invention.

FIG. 1 illustrates a preferred embodiment of the invention. The schematic view shows an ordinary railroad track having train rails 11a and 11b and rail ties 12. Train wheels 23a, 23b, 23c, and 23d are placed on, and contact, rails 11a and 11b. The train wheels may be part of a train truck carriage (or a trailering carriage).

FIG. 1 further illustrates wiring coils 22a, 22b placed around wheel axles 21a, 21b, respectively. A power generator 24 supplies current to wiring coils 22a, 22b for generating electromagnetic flux. These fluxes are preferably out of magnetic phase with each other, producing north-south opposing pairs of magnetic poles 31a, 32a and 31b, 32b. More particularly, magnetic pairs 31a, 32a of wheel axle 21a are opposite to magnetic pairs 31b, 32b of the wheel axle 21b. Therefore, wheel axles 21a, 21b and corresponding portions of rails 11a and 11b form a closed magnetic or electromagnetic circuit pattern through the contacts made by the wheels. The magnetic or electromagnetic circuit is encompassed within an area that moves along the track with the vehicle on which it is carried. The magnetic flux is continuous among magnetic pole pairs 31a, 32a, and 31b, 32b, so that the magnetic flux is smooth in the route of the closed electromagnetic circuit. Importantly, there is no electrical current to pass through the bearing assemblies from the power generator, thereby avoiding potential damage to the bearing assemblies.

Generator 24 may be powered by the locomotive prime mover, which may comprise a diesel engine or electric motor, or, alternatively, may be an internal generator that is turned by one of the wheels itself, either way thus generating the electrical current for energizing the electromagnetic circuit. It will also be noted that permanent magnets can accomplish this function by magnetizing the wheel assembly.

Monitoring means, such as a magnetometer or other flux sensor 25 is utilized to monitor the magnetic circuit pattern. In non-cracked rail areas, a magnetic flux path is induced in the wheel axle which continues through the train rail and passes back through the wheel and second axle assembly, closing a magnetic loop, namely, north pole through the rail to south pole, through the axle, to north pole etc. The flux induced in the electromagnetic circuit will be smooth and continuous if no cracked rail is encountered as the electromagnetic circuit is moved along the track.

Figure 2:
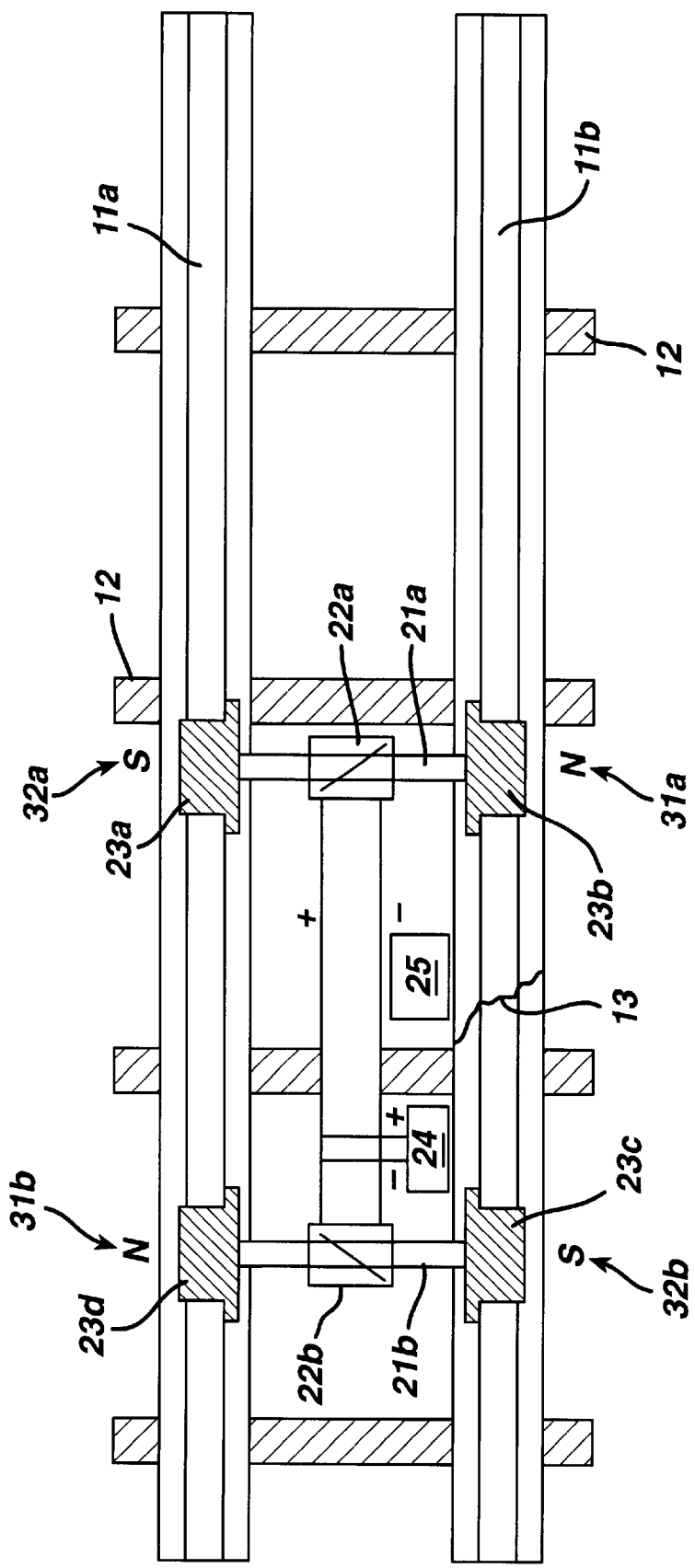
FIG. 2 is a schematic view of the invention illustrating a situation where the rail is cracked.

However, as illustrated in FIG. 2, if a crack 13 in the rail, a partially cracked rail, or other discontinuity in the rail is encountered, and the electromagnetic circuit passes over this area, an interrupted, open, or very different circuit pattern will be monitored. The flux sensor marks this discontinuity and notes its geographic location by employing, for example, a GPS (Global Positioning System) locator, odometer and track database, or the like. A ground crew can then be dispatched to investigate and repair the cracked rail. As a further refinement, the discontinuity can be compared to a track database to identify known track breaks at isolation joints which do not require repair.

Figure 3:
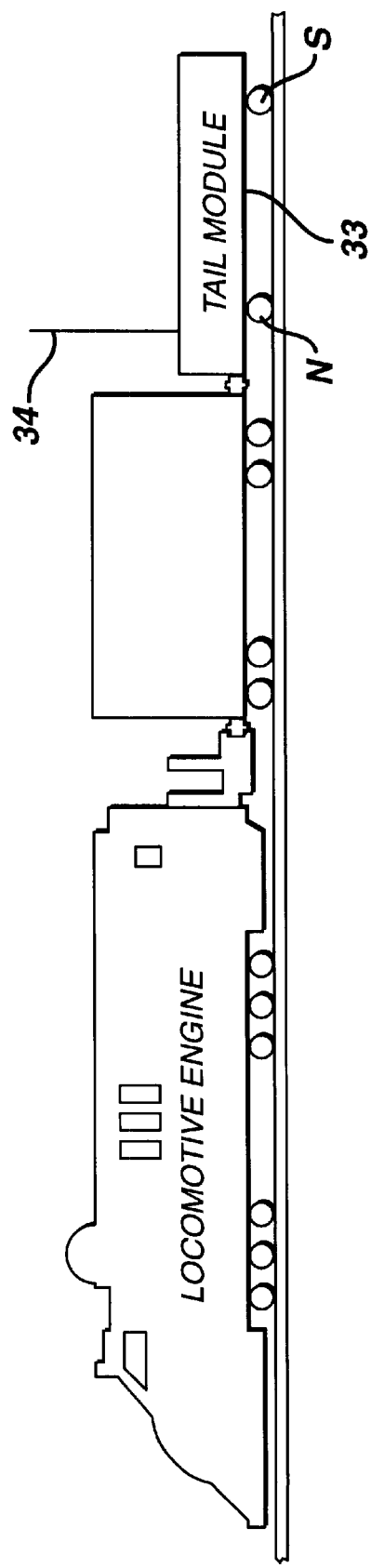
FIG. 3 is a pictorial diagram of an embodiment of the invention presented as a trailer module.

FIG. 3 illustrates application of the aforementioned procedure. The invention is implemented in a tail module 33 and powered by the locomotive engine. When a cracked rail is detected, the locating means, such as a GPS locator with an antenna 34, generates the position of the cracked rail for future inspection and repair. Tail module 33 may be placed in at various locations in the train consist; i.e., it may trail the train, as illustrated in FIG. 3, it may lead the locomotive or it may be part of the locomotive. The magnetic flux may be low so as not to pull debris inside the track area, such as loose rail spikes, etc.

Figure 4:
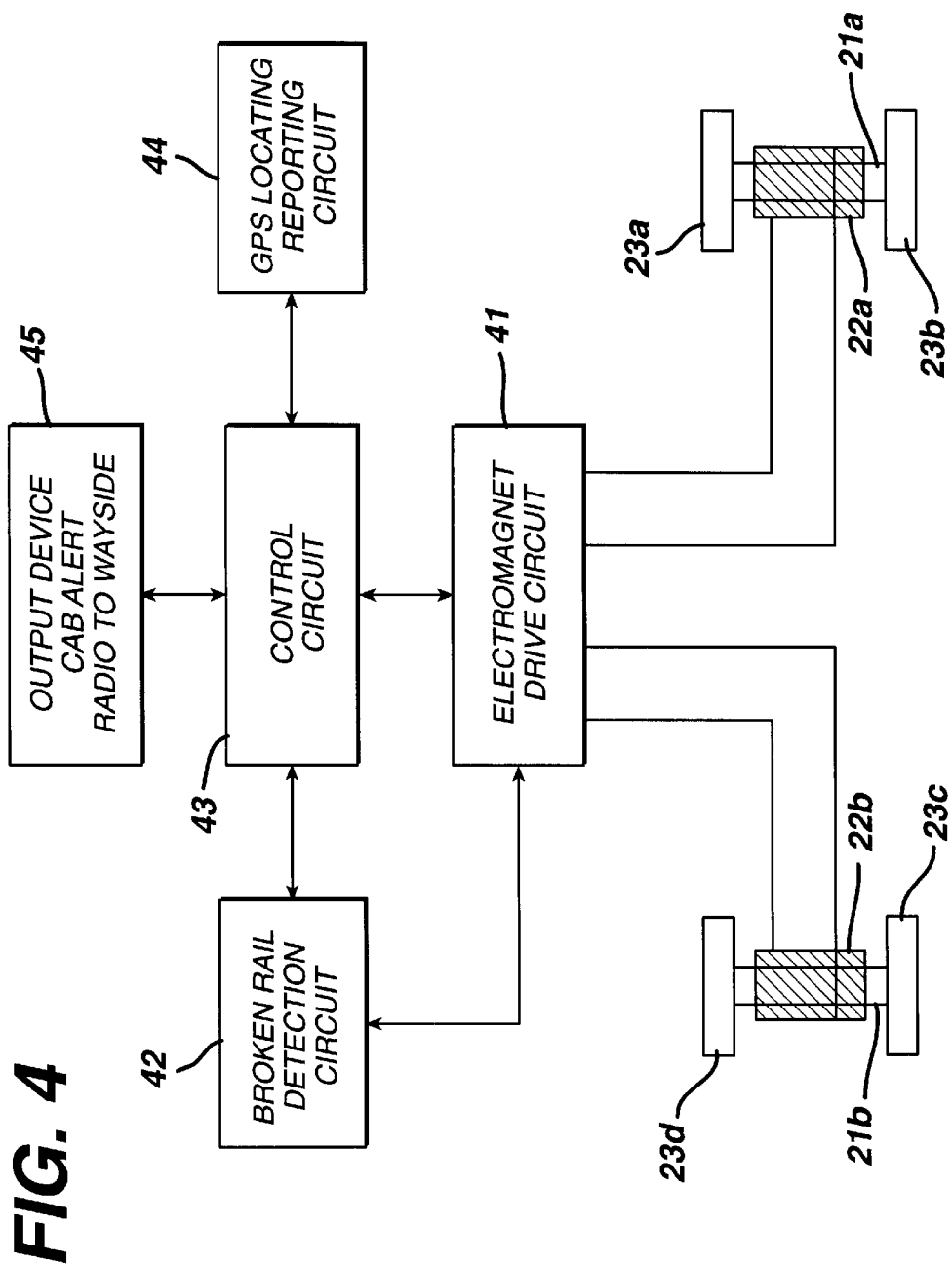
FIG. 4 is a block diagram of the system of the invention.

FIG. 4 illustrates the electrical system for detecting the broken rail. An electromagnet drive circuit 41 (including generator 24 of FIG. 1) provides the electromagnetic flux to wheel axles 21a, 21b through wiring coils 22a, 22b, respectively. Thus, through the corresponding rail and contacts made by the wheels, an electromagnetic circuit is achieved. Broken rail detection circuit 42 (e.g., flux sensor 25 of FIG. 1) monitors the electromagnetic circuit pattern to determine if the pattern is changed or interrupted. If a discontinuity or different pattern is detected, a broken rail signal is passed to a control circuit 43. Control circuit 43 acquires a position from GPS locating and reporting circuit 44, and combines and formats the broken rail signal from detection circuit 42 with the position information from the GPS locator of circuit 44. The combined and formatted signal is transferred to an output circuit 45 for producing a locomotive cab alert and/or activating a transmitter for supplying a radio signal to wayside stations.

Control circuit 43 also provides capability to increase or decrease electromagnetic flux in the wheel axles in order to prevent slippage, as described below.

Figure 5:
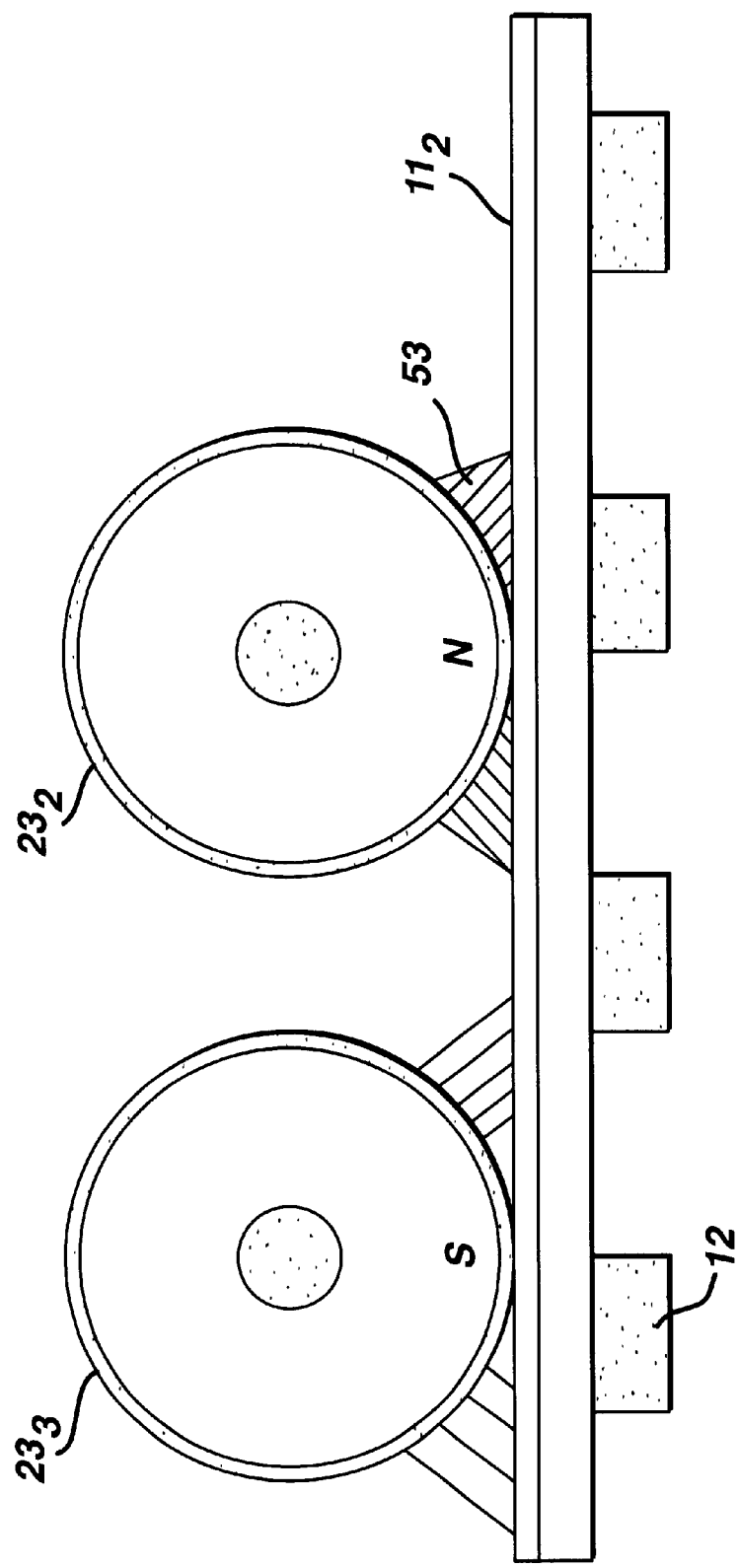
FIG. 5 illustrates the flux field expanding to the traction area.

FIG. 5 illustrates usage of the concept of "magnetraction". This principle is used to stop train wheel slippage during power pulling, downhill braking, and stationary braking. As described in conjunction with FIGS. 1 and 4, the i magnetraction force is controlled by control circuit 43, either by computer or manually when needed. Particularly, wiring coils 22a, 22b (FIG. 1) are energized when slippage is detected. Thus, electromagnetic forces are generated to stop the slippage and hold wheels 23a, 23b, 23c, and 23d tighter to the track. In this use of magnetraction wheels 23a, 23b, 23c, and 23d are the driving wheels of the locomotive.

In the use of magnetraction, the reason for the increase in traction due to the increase in magnetic flux is that the flux pattern 53, shown in FIG. 5, essentially increases the wheels traction force, due to the attractive flux field. This electromagnetic power provided to the wheels may be modulated or applied fully, depending on conditions, and may be operator or computer controlled. Basically, instead of dispensing sand on the track, as is conventionally done, electromagnetic energy is used to stop slippage and increase traction. By employing electromagnetic force to increase traction, damage to wheels and rails if slippage were to occur is avoided.

Figure 6:
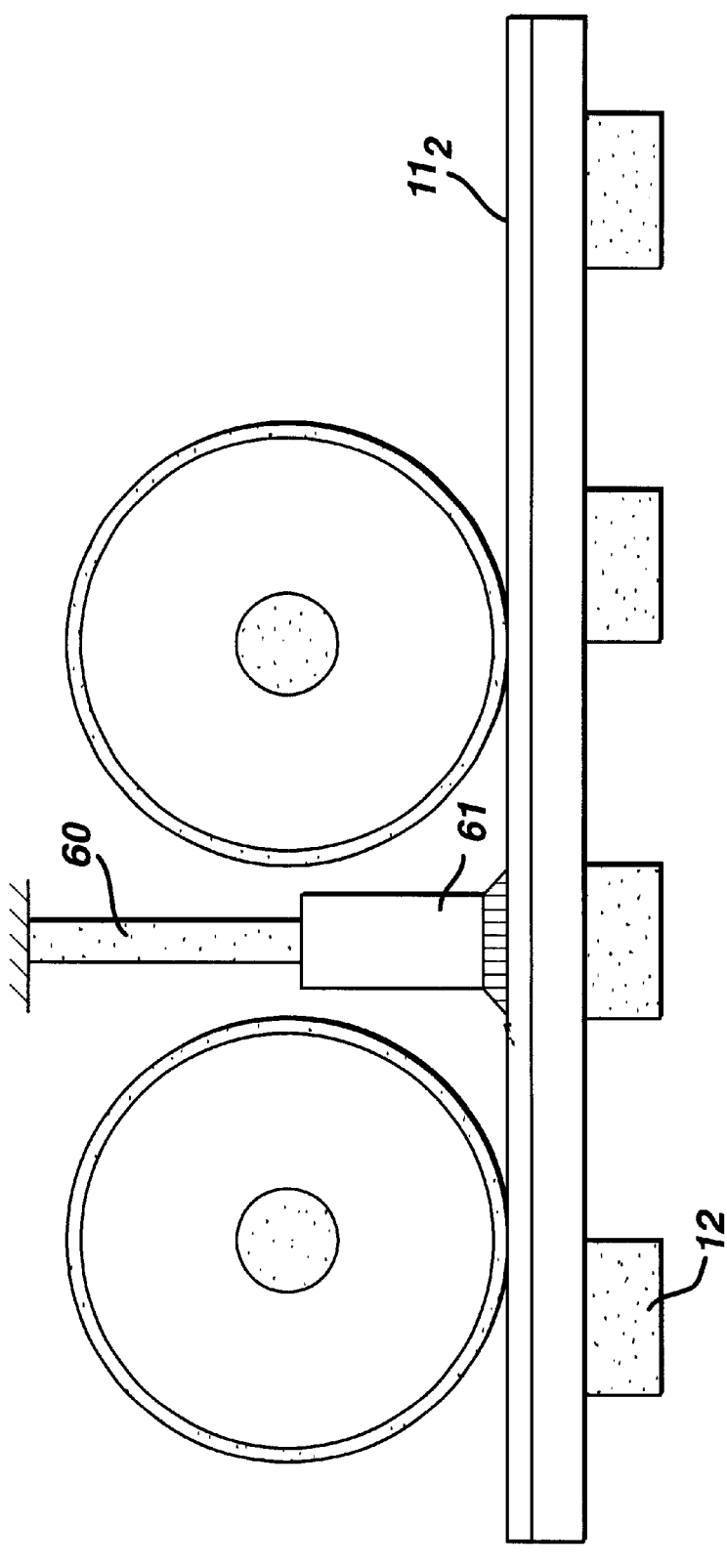
FIG. 6 is a partial schematic view of the invention employing an electromagnet for pulling the train downward to make it artificially heavier.

As shown in FIG. 6, an electromagnetic wheel loading means 60 may be employed instead of, or in addition to, including the wheels in a magnetic circuit. The wheel loading means preferably comprises an electromagnet 61 that is non-interfering with other train track functions and devices. The electromagnet pulls the train downward toward the track, making the train artificially heavier, during which time the traction increases due to the increase in friction caused by the normal force exerted by the electromagnet. The force of electromagnet 61 is controllable by control circuit 43, shown in FIG. 4. The increased traction enables locomotives to pull greater loads up steep grades. While employing electromagnetic wheel loading means 60, appropriate guards (not shown) for foreign debris, such as loose rail spikes, should be utilized.

Thus the invention enables prompt location of damage due to cracked rails and also reduces slippage. Further, the cracked rail detection is provided at high efficiency and low cost. Additional tractive effort can also be gained by use of this invention, allowing increased loads to be hauled on upgrades compared with locomotives not employing the invention.

While only certain preferred features of the invention have been illustrated and described, many modifications and changes will occur to those skilled in the art. It is, therefore, to be understood that the appended claims are intended to cover all such modifications and changes as fall within the true spirit of the invention.

What is claimed is:

1. An electromagnetic system for railroad track crack detection and traction enhancement adapted to be carried aboard a rail vehicle, said system comprising:

first and second wheel axles;

a first pair of wheels supported on said first axle;

a second pair of wheels supported on said second axle;

a first one of the wheels of said first and second pairs being adapted to contact a first rail of said railroad track;

a second one of the wheels of said first and second pairs being adapted to contact a second rail of said railroad track;

a first wiring coil wound on the first one of said axles;

a second wiring coil wound on the second one of said axles;

a power source coupled to each of said wiring coils for supplying power to produce electromagnetic flux in a magnetic circuit comprising (a.) said first pair of wheels and said first axle, (b.) said first rail, (c.) said second pair of wheels and said second axle, and (d.) said second rail; and a magnetic flux sensor for monitoring a flux pattern produced by said magnetic circuit and for generating an output indication if the flux pattern varies.

2. The electromagnetic system of claim 1 wherein said wiring coils are phased to induce opposite magnetic north-south pole pairs in each of said wheel axles and to induce opposite magnetic north-south pole pairs in each of said first one of the wheels of said first and second parirs.

3. The electromagnetic system of claim 2 further comprising means for geographically locating a position where said flux pattern is detected to vary.

4. The electromagnetic system of claim 3 wherein said means for geographically locating a position is a Global Positioning System (GPS).

5. The electromagnetic system of claim 1 further comprising electromagnetic wheel loading means coupled to said power source, for generating an artificial load imposed by said vehicle on said railroad track.

6. The electromagnetic system of claim 5 wherein said power source comprises a generator driven by rotation of a wheel on said railroad track.

7. The electromagnetic system of claim 5 wherein said wheel loading means comprises an electromagnet.

8. The electromagnetic system of claim 5 wherein said power source comprises a generator driven by a locomotive prime mover.

9. The electromagnetic system of claim 1 further comprising means for geographically locating a position where said flux pattern is detected to vary.

10. The electromagnetic system of claim 9 wherein said means for geographically locating a position is a Global Positioning System (GPS).

11. The electromagnetic system of claim 1 wherein said power source comprises a generator driven by rotation of a wheel on said railroad track.

12. The electromagnetic system of claim 1 wherein said power source comprises a generator driven by a locomotive prime mover.

13. An electromagnetic system for railroad track crack detection and traction enhancement adapted to be carried aboard a railroad locomotive, said system comprising:

first and second wheel axles;

a first pair of wheels supported on said first axle;

a second pair of wheels supported on said second axle;

a power source included on said locomotive;

electromagnetic wheel loading means coupled to said power source, for generating an artificial load imposed by said locomotive road track; and a control circuit for providing power from said power source to said wheel loading means when wheel slippage is detected during power pulling and downhill braking, and during stationary braking.

14. The electromagnetic system of claim 13 wherein said wheel loading means comprises an electromagnet.

15. A method of detecting a broken rail of a railroad track comprising the steps of:

forming a complete electromagnetic circuit joining one rail of the track at two locations on the one rail with a second rail of the track at two locations on the second rail, respectively;

moving the electromagnetic circuit along the track so as to encompass the two locations on each of said first and second rails within an area moving along the track; and detecting a change in magnetic flux in said circuit as an indication that said area encompasses at least one crack in at least one of the rails.

16. The method of claim 15 including means for geographically locating a position along the track where said at least one crack has been found.

17. The method of detecting a broken rail of claim 15 wherein said electromagnetic circuit encompasses a respective wheel contacting the track at each of the two locations on the one rail, respectively, and at each of the two locations on the second rail, respectively.

18. A method for detecting, from a moving rail vehicle, a break in either rail of a pair of rails on which said vehicle is moving, said vehicle including at least a first pair of wheels supported on a first axle and a seoncd pair of wheels supported on a second axle, said method comprising the steps of:

forming a complete magnetic circuit comprising said first and second pair of wheels, said first and second axles, and a portion of each of said rails situated between the wheels of said first pair and the wheels of said second pair, respectively;

generating constant magnetic flux within said magnetic circuit; and monitoring the magnetic flux within said magnetic circuit to detect variation in the level of said flux as an indication of a broken rail situated between the wheels of said first pair and the wheels of said second pair, respectively.

19. The method of claim 18 including the step of ascertaining a geographic location for each detected break in a rail.

20. A method of increasing friction between a railcar and a railroad track, said railcar including a source of electrical power, comprising the steps of:

detecting wheel slippage during power pulling and downhill braking; and employing said electrical power to generate an electromagnetic field between said railcar and said railroad track while said wheel slippage is detected and during stationary braking, such that said electromagnetic field acts to pull said railcar downward toward said track.

\* \* \* \* \*